United States Patent
Zhang et al.

(10) Patent No.: US 8,929,975 B2
(45) Date of Patent: Jan. 6, 2015

(54) SYSTEM FOR HEART MONITORING, CHARACTERIZATION AND ABNORMALITY DETECTION

(75) Inventors: Hongxuan Zhang, Schaumburg, IL (US); Detlef W. Koertge, Carpentersville, IL (US); Dennis Steibel, Jr., Lake Zurich, IL (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 1236 days.

(21) Appl. No.: 12/391,666

(22) Filed: Feb. 24, 2009

(65) Prior Publication Data

US 2009/0259266 A1 Oct. 15, 2009

Related U.S. Application Data (60) Provisional application No. 61/044,125, filed on Apr. 11, 2008.

(51) Int. Cl.

| | |
|---|---|
| A61B 5/04 | (2006.01) |
| A61B 5/02 | (2006.01) |
| A61B 5/0464 | (2006.01) |
| A61B 5/0452 | (2006.01) |
| A61B 5/042 | (2006.01) |
| A61B 5/0432 | (2006.01) |
| A61B 5/00 | (2006.01) |
| A61N 1/37 | (2006.01) |

(52) U.S. Cl.
CPC ............ *A61B 5/0464* (2013.01); *A61B 5/0452* (2013.01); *A61B 5/0422* (2013.01); *A61B 5/04325* (2013.01); *A61B 5/7275* (2013.01); *A61N 1/37* (2013.01)
USPC .......................................... 600/509; 600/508

(58) Field of Classification Search
USPC ................................................. 600/508–509
See application file for complete search history.

(56) References Cited

U.S. PATENT DOCUMENTS

| | | |
|---|---|---|
| 4,974,162 A | 11/1990 | Siegel et al. |
| 5,046,504 A | 9/1991 | Albert et al. |
| 5,092,341 A | 3/1992 | Kelen |
| 5,109,862 A | 5/1992 | Kelen et al. |
| 5,211,179 A | 5/1993 | Haberl et al. |
| 5,609,158 A | 3/1997 | Chan |

(Continued)

OTHER PUBLICATIONS

Porta et al., Entropy, Entropy Rate and Pattern Classification as Tools to Typify Complexity in Short Heart Period Variability Series. Nov. 2001, IEEE Transactions of Biomedical Engineering, vol. 48, No. 11, pp. 1282-1289.*

(Continued)

*Primary Examiner* — Nicole F Lavert
(74) *Attorney, Agent, or Firm* — Brennan K Bradley (57) ABSTRACT

A system analyzes and characterizes cardiac electrophysiological signals by determining instantaneous signal entropy for identifying and characterizing cardiac disorders, differentiating cardiac arrhythmias, determining pathological severity and predicting life-threatening events. A system for heart monitoring, characterization and abnormality detection, includes an acquisition device for acquiring an electrophysiological signal representing a heart beat cycle of a patient heart. A signal processor derives an entropy representative value of the acquired electrophysiological signal within a time period comprising at least a portion of a heart beat cycle of the acquired electrophysiological signal and provides an entropy value as a function of the entropy representative value and the time period. A comparator generates data representing a message for communication to a destination device in response to the entropy value exceeding a predetermined threshold.

16 Claims, 5 Drawing Sheets

(56) References Cited

U.S. PATENT DOCUMENTS

| | | | |
|---|---|---|---|
| 5,817,132 | A | 10/1998 | Karagueuzian et al. |
| 6,192,273 | B1 | 2/2001 | Igel et al. |
| 6,597,943 | B2 | 7/2003 | Taha et al. |
| 6,804,551 | B2 | 10/2004 | Griffin et al. |
| 6,993,377 | B2 | 1/2006 | Flick et al. |

OTHER PUBLICATIONS

Porta, A. Guzzetti, S. Montano, N. Furlan, R. Pagani, M. Malliani, A. Cerutti, S. , "Entropy, entropy rate, and pattern classification as tools totypify complexity in short heart period variability series", Biomedical Engineering, IEEE Transactions on, Nov. 2001, vol. 48, Issue: 11, p. 1282-1291.

Vito Latora, Michel Baranger, Andrea Rapisarda and Constantino Tsallis, "The rate of entropy increase at the edge of chaos", Physics Letters A, vol. 273, Issues 1-2, Aug. 14, 2000, pp. 97-103.

Eiichi Oida, Toshio Moritani, and Yukio Yamori, "Tone-entropy analysis on cardiac recovery after dynamic exercise", Journal of Applied Physiology, vol. 82, No. 6, pp. 1794-1801, Jun. 1997.

N. V. Thakor, Y.-S. Zhu, and K.-Y. Pan, "Ventricular tachycardia and fibrillation detection by a sequential hypothesis testing algorithm," IEEE Transactions on Biomedical Engineering, vol. 37, No. 9, pp. 837-843, 1990.

Thakor NV, Natarajan A, Tomaselli GF., "Multiway sequential hypothesis testing for tachyarrhythmia discrimination", IEEE Trans Biomed Eng. May;vol. 41, No. 5, pp. 480-487, 1994.

* cited by examiner

SYSTEM FOR HEART MONITORING, CHARACTERIZATION AND ABNORMALITY DETECTION

This is a non-provisional application of provisional application Ser. No. 61/044,125 filed Apr. 11, 2007, by H. Zhang et al.

FIELD OF THE INVENTION

This invention concerns a system for heart monitoring, characterization and abnormality detection by deriving and characterizing an entropy representative value of an acquired electrophysiological signal within a time period comprising at least a portion of a heart beat cycle.

BACKGROUND OF THE INVENTION

Cardiac arrhythmia analysis and characterization is used in the management of cardiac disorders and irregularities. Cardiac electrophysiological (EP) activities are used to sense, monitor and diagnose cardiac arrhythmia and pathology related abnormality. Such activities include, for example, P wave disorders for atrial fibrillation (AF) and ST segment changes for myocardial ischemia and infarction. However, known cardiac arrhythmia identification and analysis based on ECG signals is subjective and typically requires extensive clinical user expertise for accurate data interpretation and appropriate cardiac rhythm management. Coronary Artery Disease (CAD) and heart-related problems and cardiac arrhythmias are frequently fatal illnesses. A 12-lead electrocardiogram (ECG) and multi-channel intra-cardiac electrograms (ICEG) are a diagnostic reference standard for evaluating cardiac rhythm and events. Known waveform morphology and time domain parameter analysis of heart depolarization and repolarization, typically uses a P wave, QRS complex, ST segment or T wave, for cardiac arrhythmia monitoring and identification, e.g. atrial fibrillation (AF), myocardial ischemia (MI), ventricular tachycardia/fibrillation (VT/VF). However, the waveform morphologies and time domain parameter analysis may be subjective and time-consuming, and requires extensive expertise and clinical experience for accurate interpretation and proper cardiac rhythm management.

Some known systems apply sophisticated mathematical theories to biomedical signal interpretation, such as frequency analysis, symbolic complexity analysis and signal entropy evaluation, and focus on generating a pathology index for qualitative cardiac arrhythmia characterization. These systems typically do not determine data variance and statistical characteristics of time varying signals (ECG and ICEG). Additionally, cardiac electrophysiological activities and signals (ECG and ICEG) are time varying and known signal calculation and related analysis typically cannot localize a precise time and trend of cardiac events, such as arrhythmia occurrence.

Known cardiac signal diagnosis and interpretation systems based on an EP signal waveform and morphology, require extensive clinical knowledge and experience and provide inaccurate and subjective evaluation and diagnosis that may cause delay in cardiac rhythm management, such as drug delivery and emergency treatment. Known diagnosis and evaluation of a cardiac signal, especially ECG signals, usually use only time domain characteristics, such as voltage amplitude (e.g., ST elevation) and signal latency. Further, known system analysis of time domain parameters of an EP signal (such as a surface ECG signal), may fail to accurately characterize cardiac events or pathologies. ECG has been utilized for cardiac monitoring and is a standard clinical procedure but known ICEG signal diagnosis is not efficient when based on waveform changes, for example, since there is a lack of criteria or standards for amplitude or morphology diagnosis of ICEG signals for unipolar or bipolar cardiac activities. Time and frequency analysis may be utilized to diagnose abnormality of heart rhythms, but the analysis and monitoring fails to provide detailed information about the local myocardial tissue, such as instantaneous energy flow and instantaneous time varying complexity patterns. A system according to invention principles addresses these deficiencies and related problems.

SUMMARY OF THE INVENTION

A system analyzes and characterizes cardiac electrophysiological signals (including surface ECG signals and intra-cardiac electrograms) by performing an instantaneous signal entropy (ISE) calculation for analysis and characterizing cardiac arrhythmias and events and cardiac pathology diagnosis. A system for heart monitoring, characterization and abnormality detection, includes an acquisition device for acquiring an electrophysiological signal representing a heart beat cycle of a patient heart. A signal processor derives an entropy representative value of the acquired electrophysiological signal within a time period comprising at least a portion of a heart beat cycle of the acquired electrophysiological signal and provides an entropy value as a function of the entropy representative value and the time period. A comparator generates data representing a message for communication to a destination device in response to the entropy value exceeding a predetermined threshold.

BRIEF DESCRIPTION OF THE DRAWING

FIG. 2 shows a flowchart of a process performed by a system for heart monitoring, characterization and abnormality detection using instantaneous signal entropy (ISE) determination, according to invention principles.

DETAILED DESCRIPTION OF THE INVENTION

A system analyzes and characterizes cardiac electrophysiological signals (including surface ECG signals and intra-cardiac electrograms) based on instantaneous signal entropy (ISE) determination and analysis. The analysis involves Instantaneous signal entropy based calculation and characterization of cardiac arrhythmias and events and mapping of ISE data to cardiac pathology events for diagnosis. The system facilitates identifying cardiac disorders, differentiating cardiac arrhythmias, characterizing pathological severity, and predicting life-threatening events and also improves precision and reliability of measurement and diagnosis of cardiac electrophysiological activities.

The system ISE calculation indicates cardiac tissue status and electrophysiological function mapping for real-time application in both unipolar and bipolar modes. The system determines ISE of electrophysiological signals, characterizes the signals and provides real time ISE characteristic based pattern mapping for identifying patient health and heart function conditions. The system provides automatic real time electrophysiological signal measurement and analysis and improves the sensitivity, stability and reliability of a corresponding clinical application. Determined ISE is used for cardiac rhythm analysis and pathology diagnosis and reduces the need for extensive clinical experience and reduces subjective decision making and inaccurate cardiac rhythm management.

The system characterizes signals based on entropy theory and performs statistical (signal variance) calculations for both qualitative and quantitative characterization of cardiac activities and change in EP waveforms as well as cardiac abnormality. Real time signal variance and changes are calculated, quantified and diagnosed and provide a more precise bio-signal analysis with improved sensitivity, stability and signal to noise ratio. The system ISE calculation is used to analyze patient signals, including EP signals (surface ECG and ICEG signals) and Hemo-dynamic signals. These signals are typically not adequately diagnosed and characterized for minute pathology or event related changes in known systems. The ISE calculation quantifies time varying changes and pathological events of cardiac signals and activities and employs real time information energy calculation to diagnose cardiac activity patterns and construct an ISE based map for use in localizing a defect in cardiac tissue. The ISE analysis provides early detection and prediction of cardiac arrhythmia and pathology and supports evaluation of medical treatment and drug delivery.

Cardiac abnormalities and pathological symptoms are typically slow to appear. Some cardiac arrhythmias are even non-symptomatic and usually last a period of time before abnormal electrophysiological signals (both ECG and ICEG) demonstrate significant changes, such as ST segment elevation for more than 0.1 mV indicating ischemia. Therefore known physical diagnosis may diagnose and characterize a cardiac problem relatively late. In cardiac arrhythmia cases, pathologies and arrhythmias typically occur with some kind of signal fluctuation and distortion (mostly signal variation). For example, often there is a period of time (seconds to hours) with cardiac signal and electrophysiological activity variability before occurrence of a life threatening event. Hence instantaneous analysis of cardiac signals and response within a limited amount of time is desirable for diagnosis, detection, and prediction of cardiac arrhythmia and pathology events.

A processor as used herein is a device for executing stored machine-readable instructions for performing tasks and may comprise any one or combination of, hardware and firmware. A processor may also comprise memory storing machine-readable instructions executable for performing tasks. A processor acts upon information by manipulating, analyzing, modifying, converting or transmitting information for use by an executable procedure or an information device, and/or by routing the information to an output device. A processor may use or comprise the capabilities of a controller or microprocessor, for example. A processor may be electrically coupled with any other processor enabling interaction and/or communication there-between. A processor comprising executable instructions may be electrically coupled by being within stored executable instruction enabling interaction and/or communication with executable instructions comprising another processor. A user interface processor or generator is a known element comprising electronic circuitry or software or a combination of both for generating display images or portions thereof. A user interface comprises one or more display images enabling user interaction with a processor or other device.

An executable application comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters. A user interface (UI), as used herein, comprises one or more display images, generated by a user interface processor and enabling user interaction with a processor or other device and associated data acquisition and processing functions.

The UI also includes an executable procedure or executable application. The executable procedure or executable application conditions the user interface processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application, manipulates the UI display images in response to signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. An object or data object comprises a grouping of data, executable instructions or a combination of both or an executable procedure.

Figure 1:
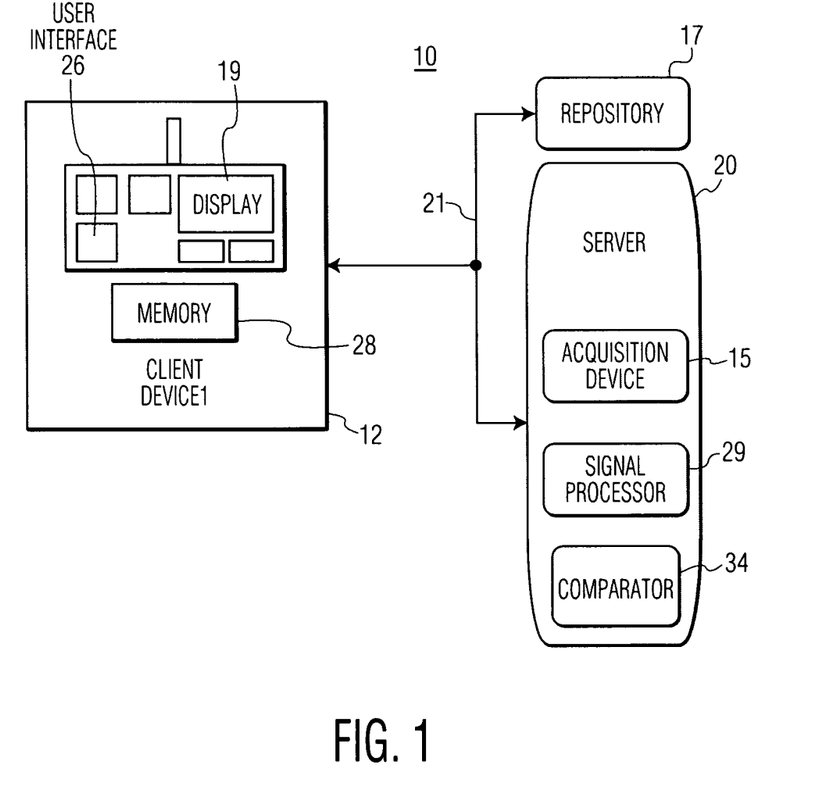
FIG. 1 shows a system for heart monitoring, characterization and abnormality detection, according to invention principles.

FIG. 1 shows system 10 for heart monitoring, characterization and abnormality detection. System 10 includes one or more processing devices (e.g., workstations, computers or portable devices such as notebooks, Personal Digital Assistants, phones) 12 that individually include memory 28, user interface 26 enabling user interaction with a Graphical User Interface (GUI) and display 19 supporting GUI and image presentation in response to predetermined user (e.g., physician) specific preferences. As well as device 12, system 10 also includes at least one repository 17, and server 20 intercommunicating via network 21. Display 19 on processing device 12 presents display images comprising a GUI. At least one repository 17 stores patient parameter data provided by patient monitoring devices, derived patient data produce by analysis and calculation and medical image studies for patients in DICOM compatible (or other) data format. A medical image study individually includes multiple image series of a patient anatomical portion which in turn individually include multiple images. Server 20 includes, acquisition device 15, signal processor 29 and comparator 34.

Acquisition device 15 acquires an electrophysiological signal representing a heart beat cycle of a patient heart. Signal processor 29 derives an entropy representative value of the acquired electrophysiological signal within a time period comprising at least a portion of a heart beat cycle of the acquired electrophysiological signal and provides an entropy value as a function of the entropy representative value and the time period. Comparator 34 generates data representing a message for communication to a destination device in response to the entropy value exceeding a predetermined threshold. System 10 performs an instantaneous signal entropy calculation (ISE) used for detection of time varying cardiac arrhythmias and real time ISE analysis based continuous monitoring and diagnosis of a patient. System 10 maps ISE calculated values to corresponding cardiac tissue medical conditions for diagnosis and pathology determination based on predetermined mapping information associating ISE value ranges, cardiac locations and corresponding medical conditions stored in mapping information in repository 17.

FIG. 2 shows a flowchart of a process performed by system 10 for heart monitoring, characterization and abnormality (including time varying arrhythmia change) detection by calculating ISE. System 10 provides instantaneous measurement and calculation of ISE for cardiac tissue and function diagnosis, including pathology severity analysis and function trend prediction. In one embodiment, ISE comprises a short time differentiation calculation of signal entropy, such as Shannon entropy.

$$H(P) = -\sum_{s \in S} P(s) \cdot \log P(s)$$

In which, S is a ROI (region of interest) time window for entropy calculation; H(P) represents uncertainty and may be used for energy and signal information integration. System 10 may perform an ISE calculation using Shannon entropy, Wavelet entropy, Tsallis entropy, for example or another type of entropy function. The system 10 instantaneous signal entropy (ISE) calculation may comprise a continuous or discrete type of computation.

Continuous ISE:

$$ISE = \underset{\Delta t \to 0}{Limit} \left\| \frac{H(P)}{\Delta t} \right\|,$$

Δt is the time window for an entropy calculation.

System 10 identifies and quantifies acute changes associated with cardiac events by calculating ISE. For example, during a PTCA (Pecutaneous Transluminal Coronary Artery) clinical procedure, there is a chance of causing acute ischemia/infarction or secondary injury. Known methods, such as ST segment voltage elevation, may not reliably detect and characterize acute injury related changes promptly Known methods usually need substantial time (5-10 minutes, or longer) to diagnose and characterize tissue defect changes based on electrophysiology (electrogram) distortion. In some cardiac cases, the signal distortion (e.g., in signal amplitude and latency) and changes caused by a PTCA procedure are not visually detectable by cardiac electrogram interpretation. In contrast ISE values support comparison of cardiac signal information and energy within a short time period.

For a random variable X with n outcomes $\{x_i : i=1, \ldots, n\}$, the Shannon entropy, is a measure of uncertainty and denoted by H(X), $$H(X) = -\sum_{i=1}^{n} p(x_i) \cdot \log_b(p(x_i))$$

In which, $p(x_i)$ is the probability mass function of outcome $x_i$. n is the number of the X data sample size and $\log_b(\bullet)$ is a logarithm calculation (typically b=2 or 10).

Applying Entropy and Information Theory Analysis to cardiac signals:

Given a sample space S and events X in S, the probability of X is written P(X) and for each data sample point, $p(x_i)$ means the probability of $x_i$ in the data space X.

The entropy is, $$H(X) = -\sum_{x} p_x \log(p_x).$$

Entropy indicates uncertainty of events but for cardiac signal analysis, pathology is usually the cause of electrophysiological signal change. Entropy H(x) may be multi dimensional and multi-channel, and may be combined and used for multi-channel signals, such as for 12 lead ECG signals with good synchronization. In this way, the sensitivity and reliability of entropy calculation is improved. Signal change typically corresponds to signal energy or power changes, hence entropy herein is deemed analogous to energy change quantification and an indication of signal mode change from normal heart rhythm to a fatal cardiac arrhythmia, for example. Note: Energy as used herein is not energy of heat or a similar energy but is broadly deemed to be signal information energy. In contrast, entropy is typically used to characterize degree of signal randomness, which typically corresponds to signal pattern and mode changes and is quantitatively and qualitatively used for cardiac pattern recognition.

FIG. 2 illustrates working mode and function flow of the system 10 (FIG. 1) ISE based calculation and cardiac monitoring. The calculated ISE improves resolution of cardiac events and pathology detection and improves sensitivity of singularity (acute cardiac abnormality) characterization. In step 205, signal processor 29 (FIG. 1) digitizes and buffers a patient monitored cardiac signal acquired by acquisition device 15 in step 203. Signal processor 29, in step 209 selects a portion of a heart beat cycle of the digitized and buffered patient monitored cardiac signal for processing such as a P wave, RR wave, QRS complex or T wave. Signal processor 29, in step 221 adaptively selects a particular type of windowed ISE calculation to be performed by selection of a window size, calculation time step and averaging method, for example. In one embodiment, the selection is automatically performed by an adaptive software process based on a user determined diagnostic analysis type and in another embodiment it is performed in response to user command. For example, for acute ischemia detection, a window size and location focused on the QRS complex and ST wave (depolarization and repolarization portion of the heart beat) is selected in step 221. For atrial fibrillation analysis, for example, an ISE window covering mostly the P wave (for atrial action examination) is selected in step 221. Signal processor 29 uses different kinds of time window for ISE calculation to improve sensitivity and accuracy of ISE analysis and reduce noise and artifact noise contribution from other portions of the cardiac signal and activities.

In step 217, signal processor 29 derives an entropy representative value (ISE), in response to at least one of, (a) a selected window size, (b) a selected calculation time step and (c) a selected averaging method. Signal processor 29 derives an entropy representative value of the digitized and buffered patient monitored cardiac signal within the selected portion of a heart beat cycle of the cardiac signal. Processor 29 provides an entropy value as a function of the entropy representative value and the time period by computing a discrete ISE:

$$ISE = \left\| \frac{H(P)_{t1} - H(P)_{t2}}{t2 - t1} \right\|,$$

windowed EntropyH(P)$_{t1}$ and H(P)$_{t2}$ overlap between time t1 and t2. The time difference between t1 and t2 comprises a window shifting step and time resolution of the ISE calculation. The time shifting step is related to accuracy of the analysis and diagnosis and may comprise a real time singularity in response to cardiac acute event detection.

Comparator 34, in step 227, compares the entropy value with one or more ranges indicated by range data stored in mapping information in repository 17 and indicative of a normal, abnormal or critical medical condition or a particular medical condition, e.g., ischemia. Comparator 34 maps ISE calculated values to corresponding cardiac medical conditions for diagnosis and pathology determination based on predetermined mapping information associating ISE value ranges, cardiac tissue locations and corresponding medical conditions stored in repository 17 as well as patient medical history and a pattern of entropy values for different cardiac tissue locations. If the entropy value does not exceed a predetermined threshold triggering an alert or lie in a range indicative of an abnormal or critical medical condition or particular medical condition, signal processor 29 changes (e.g., increases) time step t2−t1 in step 233 and repeats the entropy calculation of step 217. Steps 217, 227 and 233 are repeated for a predetermined number of iterations (e.g., 3) until a diagnosis is made or a normal condition is identified. Comparator 34, in step 229, generates data representing a message for communication to a destination device in response to the entropy value exceeding a predetermined threshold triggering an alert or indicating an abnormal or critical medical condition or identifying a particular medical condition.

Signal processor 29 calculates ISE comprising a windowed entropy value for monitoring cardiac signal changes. Compared with known amplitude based cardiac diagnosis and interpretation, the calculated ISE may capture minute signal distortion and event related changes. This advantageously reduces need for extensive clinical experience and may avoid subjective decision making and inappropriate cardiac rhythm management. The resolution of the ISE calculation is determined by a selected shifting window step. The ISE calculation uses averaging signals (for example multi-heart beat averaging with RR wave synchronization), which reduces noise and artifact effects in cardiac signals, such as electrical noise and reparation artifacts. Signal processor 29 uses a calculated sequence of ISE values of a particular anatomical location calculated on different times or occasions for deriving statistics for use in further medical evaluation and diagnosis, such as determining a substantial standard deviation indicating pathology or effects of medical drugs. In conjunction with an ISE calculation, signal processor 29 performs statistical analysis and tests to improve accuracy of qualitative and quantitative analysis and detection of cardiac events, resulting from medical treatment and drug delivery or secondary injury. This facilitates prediction of a pathology trend. Signal processor 29 performs statistical analysis including different kinds of probability analysis and statistical hypothesis test, such as a Z test, T test and sequential hypothesis test.

The calculated ISE is usable for acute cardiac pathology and event detection and for real time continuous monitoring and health on-line diagnosis and interpretation, especially for determination of cardiac incidents in a short time period. For example, acute ischemia injury events in cardiac intervention, atrial fibrillation (AF) re-occurrence and secondary injury, are precisely (in both time and event type) detected and characterized using ISE calculation based continuous monitoring.

Figure 3:
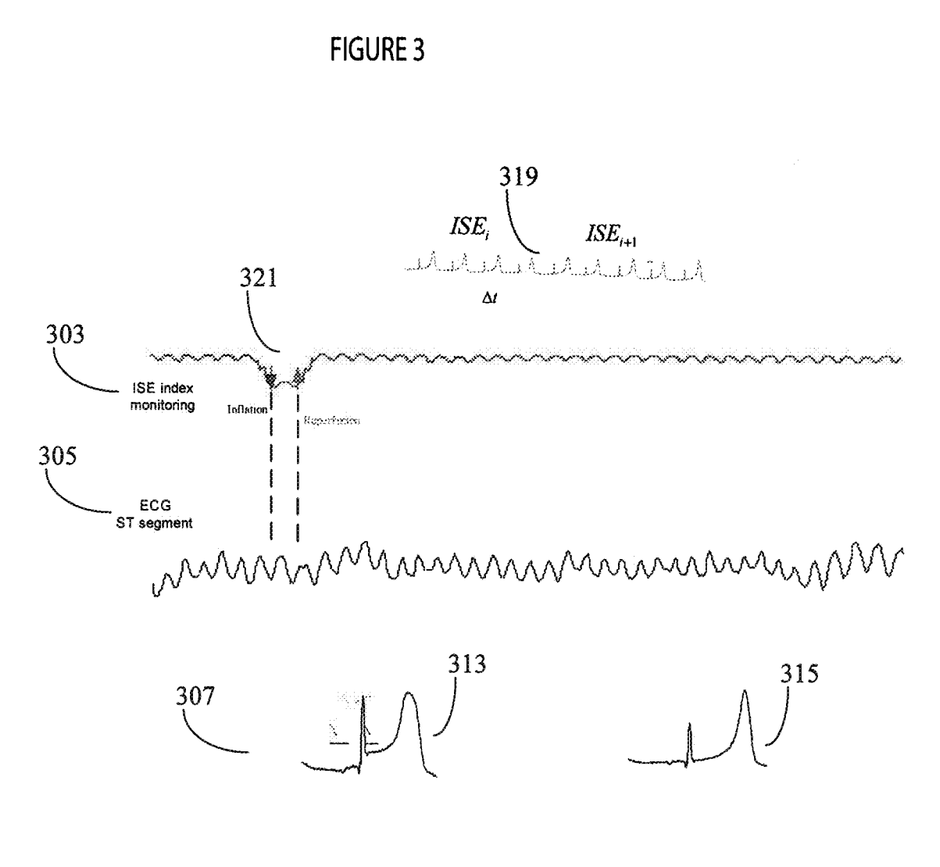
FIG. 3 illustrates instantaneous signal entropy analysis and comparison with known clinical monitoring of a heart during a clinical procedure, according to invention principles.

FIG. 3 illustrates instantaneous signal entropy analysis and comparison with known clinical monitoring of a heart during a clinical procedure. Specifically, FIG. 3 illustrates an analysis and diagnosis of a long term (several hours) clinical PTCA case based on an ISE calculation. During catheter balloon inflation (30-60 seconds), an acute ischemia, for a short period of time, may appear along with low blood flow in corresponding vessels. This kind of subtle change is usually hard to capture and localize using electrophysiological signals, such as an ECG. The time between balloon inflation and deflation (reperfusion) is about 60 seconds and inflation and reperfusion are indicated in corresponding ECG signals 313 and 315 respectively of ECG signals 307. In ECG ST segment signal 305 there is substantial signal fluctuation and noise associated with cardiac electrophysiological activities and corresponding diagnosis accuracy may decrease because of noise distortion. In contrast, the calculated ISE index monitoring signal 303 shows improved stability and sensitivity for balloon inflation and deflation events and clearly indicates the inflation-reperfusion events 321.

The ISE calculation (as illustratively represented by item 319) employs a shifting averaging window of 3 heart cycles for cardiac event and pathology analysis and diagnosis. The shifting window time step Δt is adaptively selected in response to data identifying a particular type of clinical application or medical procedure. The data and calculation window is synchronized with a detected RR wave. The synchronization and gating is adaptively expandable in response to selection of a medical application, for example, for P wave focus for atrium related analysis.

Figure 4:
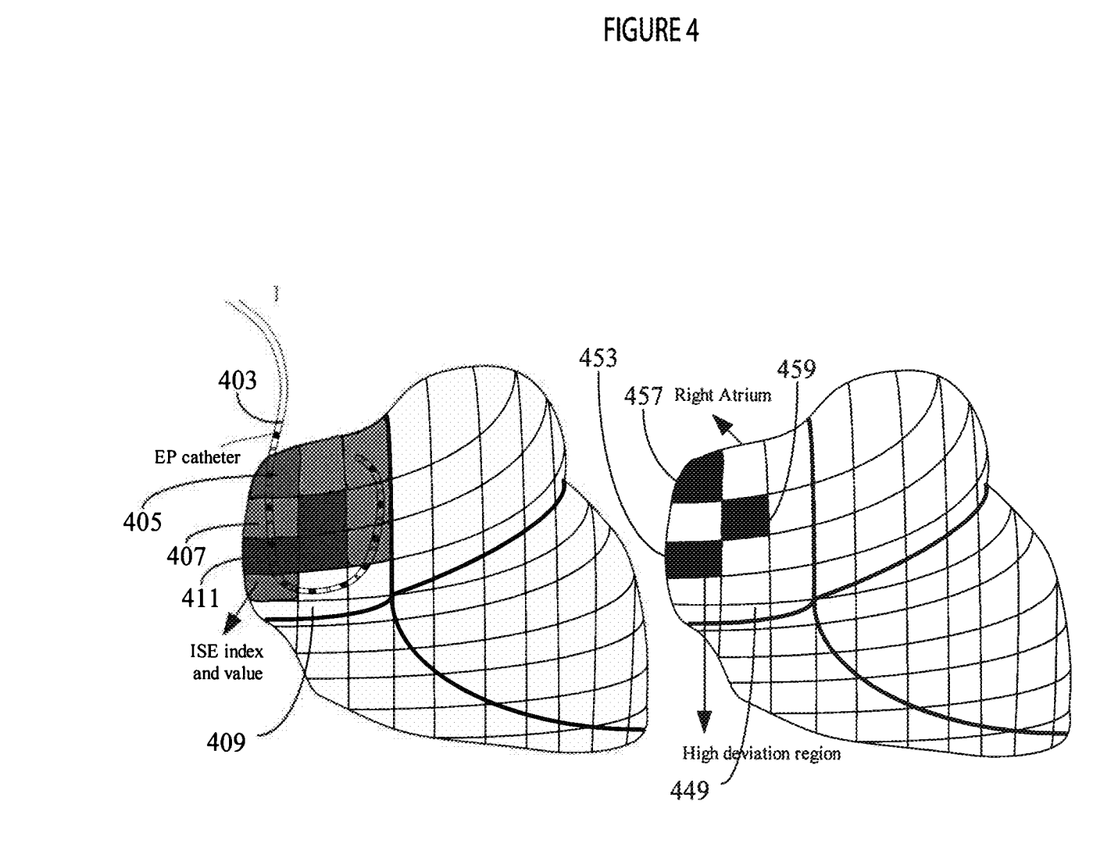
FIG. 4 illustrates pattern recognition and function mapping based on signal entropy analysis and calculation., according to invention principles.

Signal processor 29 (FIG. 1) calculates an ISE value used to analyze and characterize intra-cardiac electrograms and cardiac activities. Comparator 34 maps ISE calculated values to corresponding cardiac medical conditions for 2D (two dimensional) and 3D (three dimensional) cardiac electrophysiological activity tracking, including of signal information and energy and mode complexity, for example. FIG. 4 illustrates pattern recognition and function mapping based on signal entropy analysis and calculation. Specifically, FIG. 4 illustrates an ISE calculation based 3D signal pattern mapping and localization for real time cardiac tissue and function monitoring. System 10 (FIG. 1) employs multi-channel (channel number and spatial resolution depend on lead numbers of invasive catheters) real time ISE monitoring that provides several kinds of 3D (three dimensional) information. This information supports ISE based cardiac tissue pattern monitoring and mapping and singularity and standard deviation pattern analysis and mapping. A singularity is utilized to track an acute cardiac event with abrupt changes. Signal processor 29 determines ISE used to quantify energy and complexity of moving and stationary cardiac tissue.

Cardiac right atrium 409 and different cardiac right atrium 449 illustrate ISE calculation based pattern recognition and mapping using calculated ISE of individual tissue segments.

The ISE is calculated by signal processor 29 (FIG. 1) using electrophysiological signal data acquired using intra-cardiac catheter 403. Signal processor 29 calculates ISE of segments 405, 407 and 411, for example, of right atrium 409 using electrophysiological signals provided by multi-channel catheter 403. Right atrium 409 ISE segment values comprise a pattern of values that are used for value range comparison and pattern mapping to a medical condition using mapping information in repository 17. Also right atrium 449 illustrates a pattern of ISE standard deviation values for segments 453, 457 and 459 that may also be mapped to a medical condition using standard deviation range mapping information in repository 17. The severity of cardiac pathology indicated for the different cardiac segments may indicate a cardiac event sequence and priorities of medical treatments, drug delivery and their urgency. The ISE cardiac pattern mapping is used for real time cardiac status monitoring and cardiac event prediction as an instantaneous entropy and standard deviation range may be indicative of cardiac events. Further, an analysis and decision module such as an ANN (artificial neural network) module, Fuzzy logic module or expert system module, for example, may be used for electrophysiological pattern analysis using multi-channel ISE calculation. The analysis and decision module thereby characterizes and localizes severity of cardiac function and cardiac region impairment, predicts a pathology related event and provides information that facilitates identification of further medical treatment.

Figure 5:
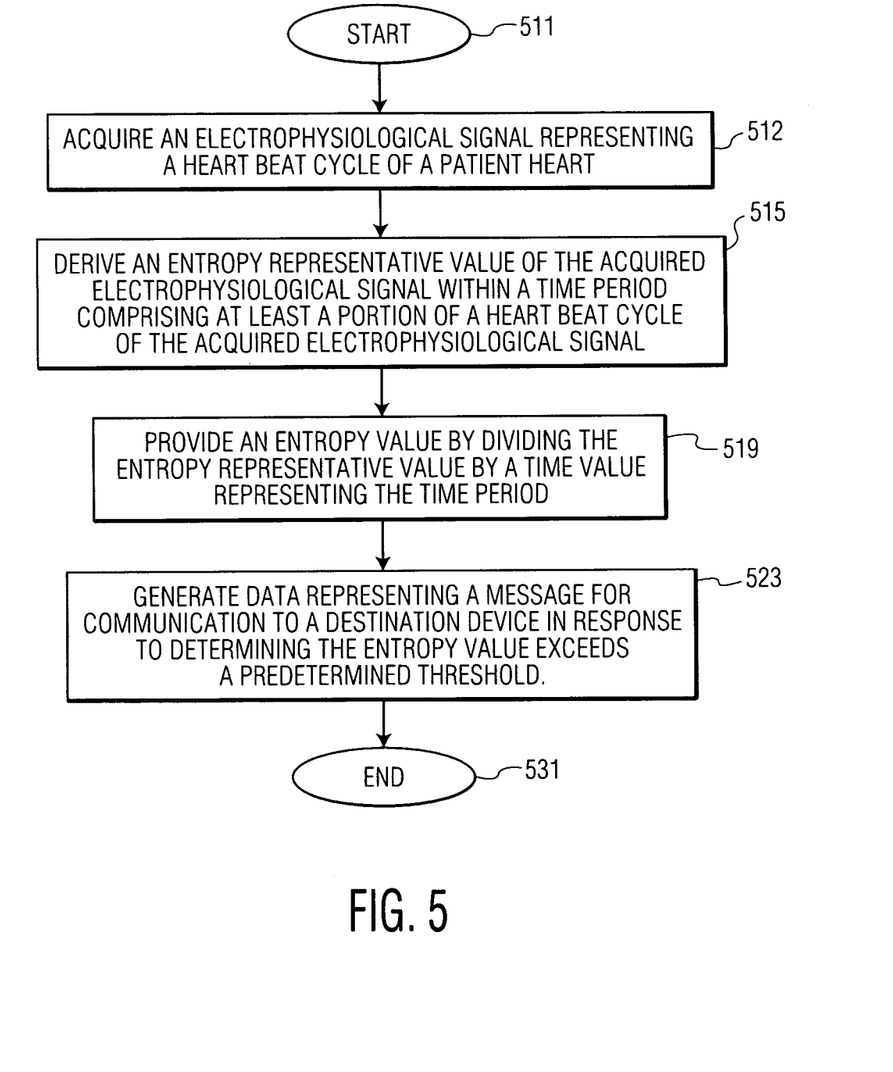
FIG. 5 shows a flowchart of a process used by a system for heart monitoring, characterization and abnormality detection, according to invention principles.

FIG. 5 shows a flowchart of a process used by system 10 (e.g., a patient monitoring device) for heart monitoring, characterization and abnormality detection. In step 512 following the start at step 511, acquisition device 15 acquires an electrophysiological signal representing a heart beat cycle of a patient heart. In step 515, signal processor 29 derives an entropy representative value of the acquired electrophysiological signal within a time period comprising at least a portion of a heart beat cycle of the acquired electrophysiological signal. Signal processor 29, in step 519, provides an entropy value by dividing the entropy representative value by a time value representing the time period. The time period comprises a window within the heart beat cycle and user interface 26 enables a user to adaptively select the window within the heart beat cycle and focus signal analysis on a particular portion of the heart beat cycle. Signal processor 29 processes the acquired electrophysiological signal to derive an entropy representative value using an instantaneous Shannon entropy (ISE) function of the form, $$ISE = \left\| \frac{H(P)_{t1} - H(P)_{t2}}{t2 - t1} \right\|,$$

where windowed Entropy $H(P)_{t1}$ and $H(P)_{t2}$ overlap between time t1 and t2. Signal processor 29 processes the acquired electrophysiological signal and provides the entropy value for a plurality of successive heart beat cycles in a continuous patient monitoring mode.

Comparator 34, in step 523 generates data representing a message for communication to a destination device in response to determining the entropy value exceeds a predetermined threshold. The message indicates severity of a cardiac condition, provides advance warning of myocardial ischemia or acute myocardial infarction in cases including non-symptomatic cases or initiates treatment by at least one of, (a) initiating drug delivery and (b) initiating electrical stimulus or pacing of a heart. Comparator 34 compares the entropy value with multiple predetermined thresholds indicating multiple predetermined signal value ranges, to identify a type of cardiac event or to characterize cardiac signal quality. Comparator 34 adaptively selects multiple predetermined thresholds in response to patient demographic information including at least one of, (a) patient height, (b) patient weight, (c) patient gender, (d) patient age and (e) patient pregnancy status. The process of FIG. 5 terminates at step 531.

The system and processes of FIGS. 1-5 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. The system calculates instantaneous signal entropy (ISE) of an electrophysiological signal to characterize cardiac arrhythmias and events and maps ISE data to cardiac pathology events to identify a diagnosis. Further, the processes and applications may, in alternative embodiments, be located on one or more (e.g., distributed) processing devices. Any of the functions and steps provided in FIGS. 1-5 may be implemented in hardware, software or a combination of both.

What is claimed is:

1. A system for heart monitoring, characterization and abnormality detection, comprising:
an acquisition device for acquiring an electrophysiological signal representing a heart beat cycle of a patient heart;
a signal processor for,
deriving an entropy representative value of the amplitude variation of the acquired electrophysiological signal within a time period comprising at least a portion of a heart beat cycle of the acquired electrophysiological signal and
using a predetermined function to process said entropy representative value and data representing said time period to provide an entropy value; and
a comparator for generating data representing a message for communication to a destination device in response to said entropy value exceeding a predetermined threshold.

2. A system according to claim 1, wherein
said signal processor divides said entropy value by the time period duration value in response to said predetermined function.

3. A system according to claim 1, wherein
said time period comprises a window within said heart beat cycle and including
a user interface enabling a user to adaptively select the window within said heart beat cycle and focus signal analysis on a particular portion of said heart beat cycle.

4. A system according to claim 1, wherein
said comparator compares said entropy value with a plurality of predetermined thresholds indicating a plurality of predetermined signal value ranges, to identify a type of cardiac event.

5. A system according to claim 1, wherein
said comparator compares said entropy value with a plurality of predetermined thresholds indicating a plurality of predetermined signal value ranges, to characterize cardiac signal quality.

6. A system according to claim 4, wherein
said comparator adaptively selects said plurality of predetermined thresholds in response to patient demographic information including at least one of, (a) patient height, (b) patient weight, (c) patient gender, (d) patient age and (e) patient pregnancy status.

7. A system according to claim 1, wherein
said signal processor processes the acquired electrophysiological signal and provides said entropy value for a plurality of successive heart beat cycles in a continuous patient monitoring mode.

8. A system according to claim 1, wherein
said signal processor processes the acquired electrophysiological signal to derive an entropy representative value using a Shannon entropy function of form, $$H(X) = -\sum_{i=1}^{n} p(x_i) \cdot \log_b(p(x_i))$$

Where, for a random variable X with n outcomes $\{x_i : i=1, \ldots, n\}$, the Shannon entropy is denoted by H(X), and $p(x_i)$ is the probability mass function of outcome $x_i$. n is the number of the X data sample size and $\log_b(\bullet)$ is a logarithm calculation (b=2 or 10 or another number).

9. A system according to claim 1, wherein
said signal processor processes the acquired electrophysiological signal to derive an entropy representative value using an instantaneous Shannon entropy (ISE) function of the form, $$ISE = \left\| \frac{H(P)_{t1} - H(P)_{t2}}{t2 - t1} \right\|,$$

where windowed Entropy $H(P)_{t1}$ and $H(P)_{t2}$ overlap between time t1 and t2.

10. A system according to claim 1, wherein
said system comprises a patient monitoring device.

11. A system according to claim 1, wherein
said message indicates severity of a cardiac condition.

12. A system according to claim 1, wherein
said message provides advance warning of myocardial ischemia or acute myocardial infarction in cases including non-symptomatic cases.

13. A system according to claim 1, wherein
said message initiates treatment by at least one of, (a) initiating drug delivery and (b) initiating electrical stimulus or pacing of a heart.

14. A system for heart monitoring, characterization and abnormality detection, comprising:
an acquisition device for acquiring an electrophysiological signal representing a heart beat cycle of a patient heart;
a signal processor for,
deriving an entropy representative value of the amplitude variation of the acquired electrophysiological signal within a time period comprising at least a portion of a heart beat cycle of the acquired electrophysiological signal and
using a predetermined function to process said entropy representative value and a time value representing the time period to provide an entropy value; and
a comparator for generating data representing a message for communication to a destination device in response to determining said entropy value exceeds a predetermined threshold.

15. A system according to claim 14, wherein
said time period comprises a window within said heart beat cycle and including
a user interface enabling a user to adaptively select the window within said heart beat cycle and focus signal analysis on a particular portion of said heart beat cycle.

16. A method for heart monitoring, characterization and abnormality detection, comprising the activities of:
acquiring an electrophysiological signal representing a heart beat cycle of a patient heart;
deriving an entropy representative value of the amplitude variation and distortion of the acquired electrophysiological signal within a time period comprising at least a portion of a heart beat cycle of the acquired electrophysiological signal and
using a predetermined function to process said entropy representative value and data representing said time period to provide an entropy value;
generating data representing a message; and
communicating the generated message to a destination device in response to said entropy value exceeding a predetermined threshold.

\* \* \* \* \*